(12) United States Patent
Boeing et al.

(10) Patent No.: US 7,970,192 B2
(45) Date of Patent: Jun. 28, 2011

(54) METHOD AND APPARATUS FOR CONTROLLING AN IMAGING MODALITY

(75) Inventors: Dieter Boeing, Erlangen (DE); Gabriel Haras, Muecke (DE)

(73) Assignee: Siemens Aktiengesellschaft, Munich (DE)

( * ) Notice: Subject to any disclaimer, the term of this patent is extended or adjusted under 35 U.S.C. 154(b) by 1521 days.

(21) Appl. No.: 11/341,508

(22) Filed: Jan. 30, 2006

(65) Prior Publication Data

US 2006/0193437 A1    Aug. 31, 2006

(30) Foreign Application Priority Data

Jan. 31, 2005  (DE) .......................... 10 2005 004 383

(51) Int. Cl.
G06K 9/00        (2006.01)
H05G 1/54        (2006.01)
A61B 8/00        (2006.01)

(52) U.S. Cl. ......... 382/131; 382/128; 378/115; 600/437

(58) Field of Classification Search .................. 382/128, 382/131; 600/437; 705/3; 378/115

See application file for complete search history.

(56) References Cited

U.S. PATENT DOCUMENTS

| | | | |
|---|---|---|---|
| 4,901,063 A * | 2/1990 | Kimura et al. | 345/530 |
| 6,944,269 B2 | 9/2005 | Schmitt | |
| 7,620,142 B1 * | 11/2009 | Toth | 378/16 |
| 7,657,074 B2 * | 2/2010 | Haras | 382/131 |
| 2002/0176530 A1 * | 11/2002 | Okumura et al. | 378/19 |
| 2003/0108154 A1 | 6/2003 | Schmitt | |
| 2006/0065844 A1 * | 3/2006 | Zelakiewicz et al. | 250/370.09 |
| 2006/0264749 A1 * | 11/2006 | Weiner et al. | 600/437 |
| 2007/0222789 A1 * | 9/2007 | Yoshio et al. | 345/589 |

FOREIGN PATENT DOCUMENTS

| | | | |
|---|---|---|---|
| DE | 101 60 611 A1 | 6/2003 | |
| WO | WO 2005091011 A1 * | 9/2005 | |

OTHER PUBLICATIONS

English language translation of a Chinese Patent Office Action for Chinese Patent Application No. 200610006791.4.

* cited by examiner

*Primary Examiner* — Brian P Werner
*Assistant Examiner* — Nirav G Patel
(74) *Attorney, Agent, or Firm* — Harness, Dickey & Pierce, P.L.C.

(57) ABSTRACT

A method is described for controlling an imaging modality. The method includes acquiring data specific to an examination object and automatically selecting a raw data record from a number of raw data records on the basis of the data specific to the examination object. The method further includes producing an image on the basis of the selected raw data record and by using a selected control parameter set. The produced image is then output to a user. Thereafter, a change command of the user is detected, for altering the control parameter set, or detecting a confirmation command for confirming the control parameter set. Next, the control parameter set is changed in accordance with a detected change command. The method then includes repeating the method steps of producing, outputting, detecting and changing with the respectively current, changed control parameter set until a confirmation signal is detected. Finally, image data is acquired by using the current control parameter set when a confirmation command is detected. An apparatus suitable for controlling an imaging modality is also described.

32 Claims, 3 Drawing Sheets

METHOD AND APPARATUS FOR CONTROLLING AN IMAGING MODALITY

The present application hereby claims priority under 35 U.S.C. §119 on German patent application number DE 10 2005 004 383.6 filed Jan. 31, 2005, the entire contents of which is hereby incorporated herein by reference.

FIELD

The invention generally relates to a method for controlling an imaging modality, in particular for controlling a computed tomography system. The invention also generally relates to a corresponding apparatus for controlling an imaging modality and to such a modality, in particular a computed tomography system, having a corresponding apparatus.

BACKGROUND

Various imaging methods are known in modern medicine for obtaining a comprehensive knowledge of specific organs and their conditions essentially without opening the body. X-ray systems, computed tomography systems, magnetic resonance systems and ultrasound systems are examples of appropriate imaging systems. Such systems and/or units are usually denoted as modalities.

A multiplicity of control parameters must be adjusted in order to use an imaging modality in order to obtain sufficiently good images of a structure and/or an organ, for example a bone structure, the brain, the heart, the lung, the gastrointestinal area etc for a specific set of questions forming the basis of the examination. Thus, for example, it is necessary to adjust the most varied technical control parameters such as voltage, current, slice thickness, pitch, rotational speed etc in the case of computed tomography systems. In the case of systems of recent generations, it is becoming ever more complex to adjust all the control parameters optimally.

In order to carry out an examination in a way that is as friendly as possible to the patient, the control parameters should be adjusted during the examination such that the images produced exhibit an image quality sufficient for the respective examination in conjunction with as low a radiation dose as possible. In this case, there should be a high measure of operator friendliness. In order to avoid errors as far possible during adjustment, the operation should advantageously proceed as intuitively as possible.

Modern imaging systems already offer for the most varied body regions selected measurement protocols that prescribe specific control parameter sets for the various types of examination and/or for the clinical problems on which the examination is based. Thus, for example, in the meantime substantially more than 100 different protocols are available on computed tomography systems in the high-end region, for example. The various measurement protocols then further require to be adapted manually to the precise examination problem and to the patient-specific geometry.

In particular, in the case of a computed tomography system, for example, the tube current, and thus the dose—must be adapted to the so-called patient profile, that is to say to the size and the weight of the patient. This is because the attenuation, and thus the image quality, depends on the thickness of the patient's body in the beam direction. Thus, given a relatively strong patient profile there is a need for a relatively high tube current in order to achieve the same image quality as in the case of a relatively thin patient profile. Even in the most modern systems, it has only been possible to date to automatically fit the tube current, but not the tube voltage, for example, to the patient profile.

As a rule, an operator of such a system selects and adapts the suitable protocols on the basis of his experience with such examinations. It can therefore by all means occur with inexperienced examiners that insufficient examination results are obtained owing to unfavorable parameter constellations. In the extreme case, this can necessitate a repetition of the examination given an excessively low image quality. The additional radiation burden caused thereby in a computed tomography system, for example, is not inconsiderable for the patient.

The same holds in the case of magnetic resonance examinations, where the patient is exposed to an additional unnecessary high-frequency burden. On the other hand, even an excessively high image quality that is not required per se for the examination that is to be carried out, because it is associated with no additional gain of information, or only a very slight one, leads only to an additional burden for the patient. Added to this in the case of computed tomography examinations and, in particular, magnetic resonance examinations is the fact that measurements that may have been carried out with an unnecessarily high image quality lead to an unnecessarily long measuring time, and this renders the measurement as a whole more expensive.

SUMMARY

It is therefore an object of at least one embodiment of the present invention to provide a method and/or an apparatus for controlling an imaging modality such that even inexperienced operators can produce better and even optimal images for the problems on which the examination is based in a simple and even in the simplest possible way, together with a dose that is as low as possible.

The method according to at least one embodiment of the invention in this case includes the following method steps:

Firstly, data specific to the examination object such as, for example, the age, the weight, the sex of the patient as well as further measures such as, for example, the overall size of the patient or of the body part to be examined are acquired. There then follows an automatic selection of an example raw data record from a number of example raw data records on the basis of the data specific to the examination object. An example image is then produced on the basis of this example raw data record by using a selected control parameter set.

The selection of the initial "start" control parameter set is preferably performed in this case by taking account of the selected measurement protocol. The example image, which conveys an advance impression of the image quality to be expected to the examiner, is then output to the user. Subsequently, change commands of the user for the purpose of altering the control parameter set, or a confirmation command for confirming the control parameter set are detected. If a change command is detected, the control parameter set is changed according to this change command.

An updated example image is then produced for the new control parameter set, and output again to the user, and further change commands of the user and/or a confirmation command of the user are detected. These method steps are repeated with the respectively current, changed control parameter set until a confirmation signal of the user is detected. Finally, when such a confirmation signal is detected the acquisition of image data is performed with the aid of the modality by using the current control parameter set, that is to say the imaging modality is driven with the aid of this control parameter set in order to acquire the image data.

A corresponding apparatus, for example, for controlling an imaging modality includes the following components for this purpose:

An interface for acquiring data specific to the examination object. This can be, for example, a user interface having a keyboard or the like, via which the data specific to the examination object are input. However, it is also possible for this to be a network interface in order, for example, to take over patient data already present in a radiological information system (RIS). It can also likewise be an internal interface in order, for example, to acquire suitable data specific to the examination object by evaluating existing images of the examination object, a memory device with a number of example raw data records. This memory device can be integrated in the control apparatus specifically for this purpose. It can also likewise be a general memory device, for example an external memory device in a PACS (Picture Archiving and Communication System), a specific memory area that can be accessed by the control apparatus being available for the example raw data records, for example, a selection device for selecting an example raw data record from the number of example raw data records on the basis of the data specific to the examination object, an image reconstruction device for producing an example image on the basis of the example raw data record and by using a selected control parameter set. Use can (also) be made here of an appropriately configured image reconstruction device that otherwise serves for reconstructing the "true" images from the acquired raw image data, a user interface for outputting the example image to a user and for detecting a change command of the user for altering the control parameter set, and/or a confirmation command for confirming the control parameter set. This user interface can also be constructed from a number of components, a parameter modification device for changing the control parameter set on the basis of a detected change command, an image data acquisition interface for acquiring image data by using a current control parameter set. This image data acquisition interface uses the current control parameters to drive the components of the respective modality that are required to acquire the image data—in the case of a computer tomograph, for example, the table drive, the gantry drive, the X-ray source and the detector.

The inventive control method or the control apparatus of at least one embodiment can be used to explain directly to the respective operator the image quality that can be achieved by varying particular control parameters. This provides an extreme simplification of the parameter selection and thus of the examination planning, such that even very inexperienced users can produce images of sufficient quality such as are required for the respective examination without setting an unnecessarily high dose, for example.

The further description respectively include particularly advantageous refinements and developments of embodiments of the invention. In this case, the apparatus according to at least one embodiment of the invention can also be developed in accordance with the method, and vice versa.

In order to produce an example image, it is particularly preferred for an image of at least one region of interest of the examination object that has been reconstructed on the basis of the example raw data record with regard to an optimized image quality, to be modified as a function of the current parameter set in such a way that the example image reproduces the image quality achievable with the current parameter set. The modification is performed in this case in such a way that, for example, the example raw data record is correspondingly noisy when the dose is lowered in order to represent the altered noise impression occasioned by the lowering of the dose.

It is likewise possible, for example, to simulate in the example image artifacts or other effects to be expected upon alteration of the dose or other parameters.

The simulation is based in this case on an example raw data record that has been selected as aptly as possible for the respective patient—in particular for the patient profile actually present—and for the type of examination to be undertaken. It is thereby ensured that the simulation is as realistic as possible, and thus that the operator can see in advance precisely which images he can achieve with the particular image quality when measuring with the aid of the adjusted parameter set.

A portion of the data specific to the examination object and which are to be used to select the example raw data record, such as, for example, the age and the weight of the patient and the examination region, can be acquired, by way of example, as early as when registering the patient, and be taken over by a radiological information system. However, it is preferred in addition to acquire suitable data specific to the examination object for use when selecting the example raw data record with the aid of previously taken pictures of the examination object.

These previously taken pictures can be, for example, so-called "topograms" (overview pictures) of the patient. Such topograms are usually taken in any case for planning the examination. Here, the topograms can be evaluated automatically within the scope of at least one embodiment of the present invention, for example to determine the exact patient profile, which can be utilized both when selecting the example raw data record and during the later modification of the example images, in particular during noisification of the image in order to simulate the image quality as a function of the adjusted dose. Alternatively, or in addition to such topograms, it is also possible to use pictures from previous examinations that are taken from archives or databases, for example.

The selection of the example raw data record is also preferably performed by taking account of data specific to the examination, that is to say by taking account of information relating to the type of examination and/or the nature of the examination, for example whether it is a running examination, a contrast medium examination and/or the particular problems on which the examination is based. These data specific to the examination are also acquired as a rule as early as during patient registration and can—as far as they are available—be taken over by an RIS.

The example raw data record can therefore be selected in a fully automatic fashion without any interaction by the user.

In a further preferred variant, it is possible to make use as example raw data record of a raw data record from a previous examination of the relevant current examination object. For this purpose, the raw data records of specific examinations are preferably temporarily entered into a database automatically in common with further information relating to the examination.

If the patient concerned is to be examined anew, and such prior investigations are to hand or stored for the region of interest, these raw data records can be used for the following examinations in order to produce the example images therefrom. An example image reconstructed from an example raw data record originating from the patient himself then corresponds to the patient to be examined or to the examination object.

This method can be applied, in particular, when there is a multiphase examination such as, for example, a contrast medium examination in the case of which an examination is initially performed without contrast medium in the first examination phase, and then examination with contrast medium is performed in a second examination phase. In this case, the raw data of the native examination can be stored temporarily at the user's wish as exemplary raw data for use of the example images in the subsequent examination phases.

Of course, instead of only one example image, it is also possible to take a number of example images by taking account of the respectively current control parameter set. For example, a number of slices can be taken in various directions through the region of interest in the examination object. However, since the production of the example images requires a certain computing time, in most instances only one exemplary image is produced—as long as there is no need for a number of images in order to reproduce the situation. It is therefore assumed as a rule in this document, without limiting the invention to such a case, that a single example image is produced.

In addition to the example image, at least a portion of the parameters, preferably all the parameters relevant to image quality, of the current control parameter set is indicated to the user and offered for alteration. For this purpose, the user interface of the apparatus according to at least one embodiment of the invention preferably has a graphic user interface having at least one drive device(s) that is designed in such a way that the example image is displayed on the user interface for the purpose of adjusting the control parameter set and, at the same time, at least a portion of the parameters of the current control parameter set are displayed to the user and offered for alteration. This can be performed in different areas of the user interface, for example on various "index cards" that can, for example, be called up in the usual way with cursors by using a mouse or similar. The user interface can fundamentally also extend to various components. Thus, the control apparatus can have a number of screens, for example, the example image being displayed on one screen, and a user interface area with the parameters being displayed on another screen or another display unit.

It is particularly preferred to display at least one current dose parameter and/or one current image quality parameter to the user for example on the user interface, and to offer them/it for alteration. These two parameters interact particularly strongly. In addition, the parameters directly influencing the examination result and the burden on the patient are involved here.

Upon detection of a dose parameter change command that is intended to lead to a change in the current dose, the parameter set is then preferably altered automatically such that a maximum image quality is achieved for a specific dose fixed by the dose parameter change command. That is to say, in the case of a CT system, for example, not only is there an adjustment of the tube current essential to the dose, but at the same time the other parameters, such as table feed, slice thickness etc are adapted such that the image quality is optimized while maintaining of the dose. Consequently, all the parameters are adapted correspondingly to the dose to be expected in the case of such a "dose-oriented parameter adaptation".

Likewise, upon detection of an image quality change command that is intended to lead to a change in the current image quality, it is preferred for all the necessary parameters of the parameter set to be altered automatically such that the current image quality is changed in accordance with the image quality change command. This can be performed, for example, by reducing or increasing the dose or else by altering other parameters such as the slice thickness or the table feed. In the case of such an "image quality oriented parameter adaptation" it is preferably ensured that all the parameters are adjusted such that the adjusted image quality is achieved with the smallest possible dose by firstly optimizing all the remaining parameters.

In a particular example embodiment, it is displayed, together with the display of a parameter, in particular the dose parameter or the image quality parameter, whether the relevant parameter lies in a specific standard range—with reference to the respective nature of the examination and the available patient data, in particular the patient profile. This standard range can preferably be defined in advance by the user, that is to say an experienced operator of a modality can, for example, fix in advance which values are acceptable for particular conditions. It is then signaled to other operators on this unit, by specifying the position of the parameters inside the defined standard range, whether they are working with acceptable values, or whether the adjustment of the parameters should be yet further improved before carrying out the examination.

In a particularly preferred variant for this purpose, the at least one drive device(s) of the user interface is designed in such a way that the adjustable parameters are respectively displayed in the form of a marker that can be adjusted with the aid of a pointer unit—for example a mouse—on the graphic user interface. In this case, the relevant parameter is respectively assigned a graphic scaling element.

By placing the marker relative to the scaling element, it is then indicated whether the relevant parameter lies in the defined standard range. The marker can, for example, be a simulated linear regulator that is stored with the aid of a color variation scale. In this process, the color variation of the various color ranges mark whether a standard range is involved, a range in which the parameters are adjusted too high, or a range in which the parameter value is too low.

BRIEF DESCRIPTION OF THE DRAWINGS

Example embodiments of the invention are explained below in more detail with reference to the attached figures. In the drawings.

DETAILED DESCRIPTION OF THE EXAMPLE EMBODIMENTS

Figure 1:
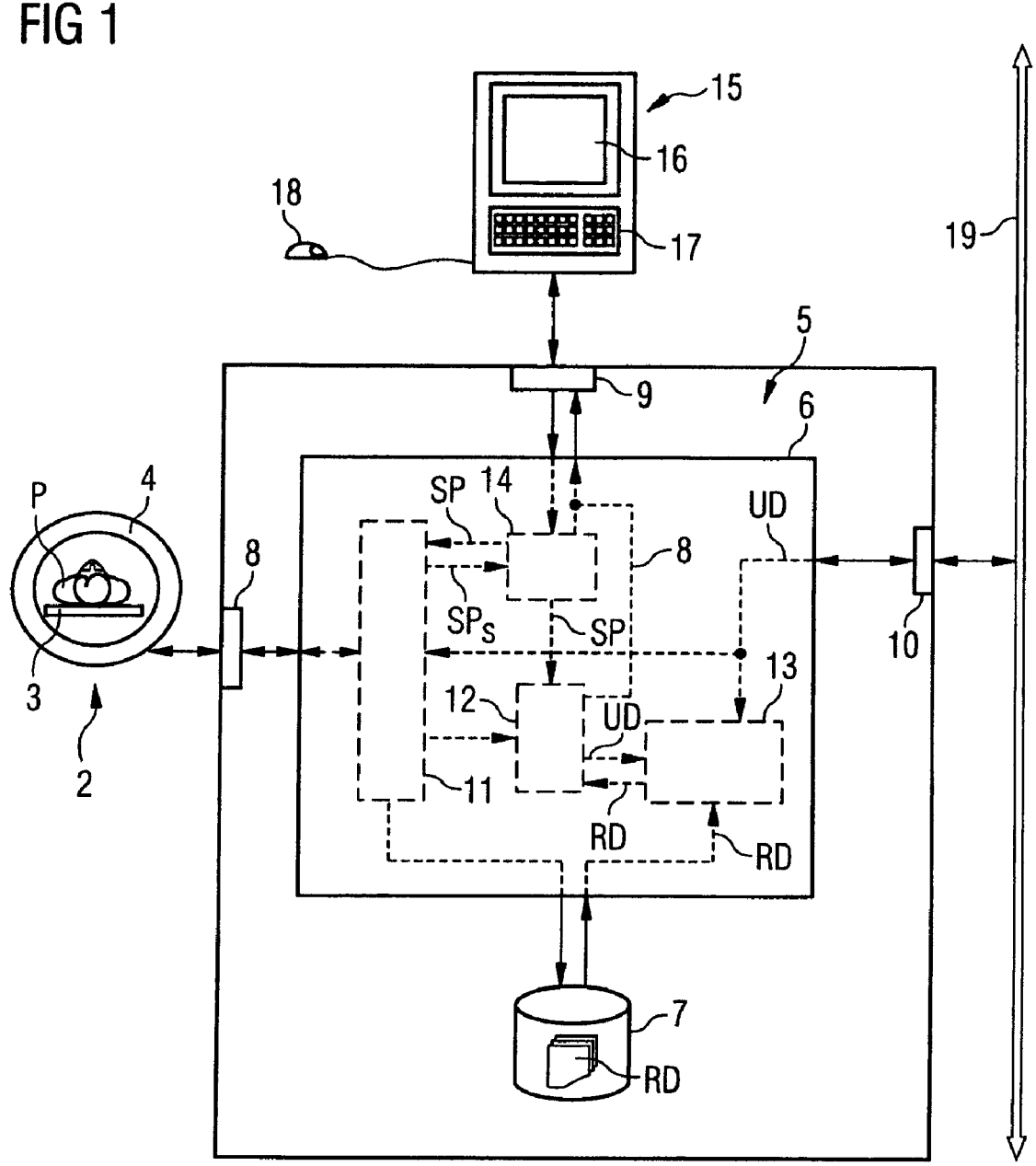
FIG. 1 shows a schematic of a computed tomography system having a control apparatus according to at least one embodiment of the invention.

The example embodiment illustrated in FIG. 1 of an inventive modality 1 is a computed tomography system 1.

The main components of such a system 1 are, firstly, the actual image data acquiring unit 2, the so-called "scanner" 2, of which here there is illustrated only schematically a gantry housing 4 and a table 3 that can be moved through the annular gantry housing 4 and on which a patient P is supported for examination.

This scanner 2 is driven by a control apparatus 5. This control apparatus 5 has a programmable processor 6 on which essential control components inter alia for driving the scanner 2 are implemented in the form of software. The control apparatus 5 is coupled to the scanner 2 via a drive interface 8 such that the parameters or signals required for control are passed to the scanner 2, and the acquired raw image data can be taken over by the scanner 2. The raw image data are then further processed inside the control apparatus 5.

Moreover, the control apparatus 5 is also connected by way of an I/O interface 9 to a user interface 15 in the form here of a conventional terminal 15 with a keyboard 17, a display 16 and a pointer unit 18 (here a mouse 18). The examining person can use this terminal 15 to operate the control apparatus 5 and thus the scanner 2, as well as all the further components of the computed tomography system 1.

The control apparatus 5 is connected to a bus 19 of a radiological information system via a network interface 10.

The control apparatus 5 further has a memory 7. Stored inter alia in the memory 7 are exemplary raw data records RD that can be used to carry out the method according to at least one embodiment of the invention.

Implemented on the processor 6, inter alia, as an essential component is an image data acquisition device 11 that serves the purpose of driving the scanner 2 via the drive interface 8 with the aid of specific control parameters, and therefore ensures that the appropriate control signals are sent to the scanner 2, and that raw image data arriving via the drive interface 8 are acquired and preprocessed. These raw image data are then passed to an image reconstruction device 12 that reconstructs the desired tomograms from the raw image data. This image reconstruction unit 12 is also implemented on the processor 6 in the form of software.

Implemented on the processor 6 as further components of at least one embodiment of the invention are a selection device 13 for selecting an exemplary raw data record RD from the memory 7, and a parameter modification device 14 by which a control parameter set SP, $SP_s$ can be changed as a function of change commands that the user can input via the user interface 15. It will be explained in more detail below how these different components cooperate precisely in order to carry out the method according to at least one embodiment of the invention.

It is clear that in addition to the components illustrated the computed tomography system 1 also has all further components that such a system usually includes for proper use. However, for the purpose of greater clarity these components are not illustrated in FIG. 1.

Figure 2:
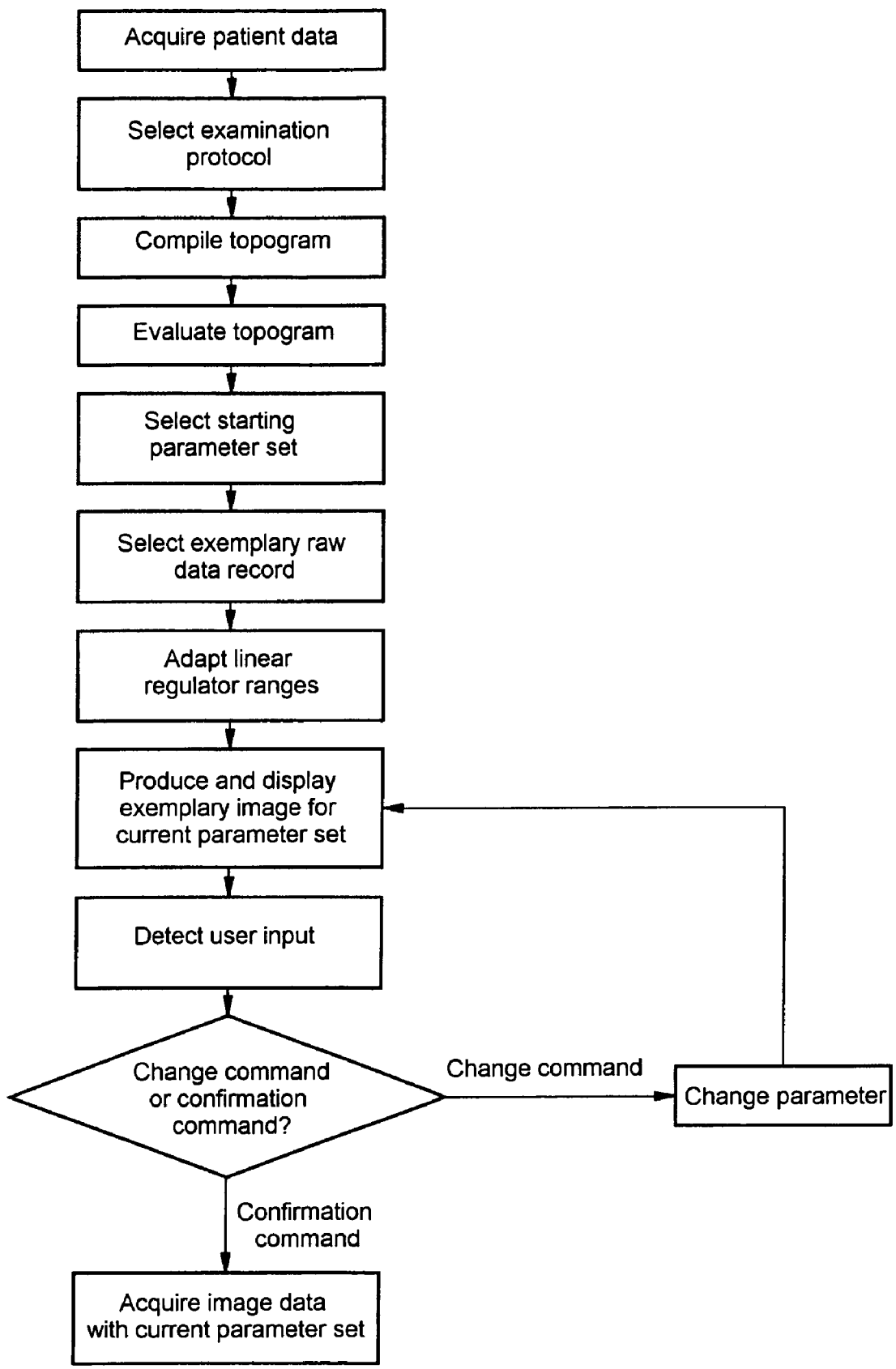
FIG. 2 shows a flowchart of a possible cycle of the control method according to at least one embodiment of the invention.

FIG. 2 shows a possible cycle of the control method according to at least one embodiment of the invention for an examination, from the acquisition of the patient data up to the image data acquisition.

The necessary patient data are firstly acquired here in a first step. The master patient data are usually already acquired before the examination during the course of registration when admitting the patient to the organization, for example the hospital or the X-ray practice to which the computer tomograph belongs. The data can be retrieved via the RIS, here via the bus 19, for example, and are then available in a so-called work list on the computed tomography system. Further patient data can be supplemented on the spot shortly before the examination. For example, the weight of the patient and/or the size can be added.

A suitable examination protocol is then selected in a further step, it being decided, inter alia, what is the nature of examination involved, which body region is to be examined and in which position the patient is to be supported on the table. A topogram of the patient P can be compiled in the usual way subsequently. These first three method steps do not differ per se from the conventional methods such as have been carried out to date in order to execute an examination by computer tomograph, this topogram having been used so far only for the purpose of manual planning of the further examination, this being done by inserting the scanning region into the topogram.

However, in the cycle illustrated in FIG. 2 the topogram data are automatically evaluated, it being calculated, inter alia, what is the attenuation of the X-rays to be expected in the various slices through the examination object. The results of this calculation are, inter alia, the basis for further automatic decisions within the method. Thus, for example, by taking account of these data and on the basis of the selected examination protocol it is possible to assemble and/or select a parameter set that is firstly proposed to the operator as a suitable parameter set for the examination to be carried out, and which serves as "starting parameter set" $SP_s$ in the subsequent method steps. This starting parameter set $SP_s$ can be compiled, for example, by the image data acquisition device 11 on the basis of the selected examination protocol, and passed onto to a parameter modification unit 14, which will be explained in more detail later.

Moreover, a decision matrix with the aid of which the example raw data record most comparable to the current case is selected, can be set up on the basis of the topogram evaluations together with the age, the weight and the sex of the patient as well as information relating to the body region being examined, or on the basis of further data specific to the examination object. If, for example, it is specified when inputting for the purpose of selecting the examination protocol that a contrast medium examination or progress monitoring applies, an appropriate exemplary raw data record is selected—if appropriate data are available.

The acquisition of the image data for compiling the topogram is then performed with the aid of the image data acquisition device 11 (see FIG. 1). The reconstruction of the topogram is carried out in the image reconstruction unit 12. The topogram can then be passed on for further evaluation to the selection device 13 which, for example, firstly carries out the topogram evaluation and furthermore uses the data specific to the examination object obtained in the process, together with the further data UD that are specific to the examination object and which the selection device 13 obtains, for example, via the network interface 10 and the bus 19, or via the I/O interface 9 and the user interface 15, to select the example raw data records RD from the memory 7.

All the information that the operator must prescribe to the system can be input via the user interface 15. A graphic user interface 20 is made available for this purpose, for example on the screen 16 of the user interface 15.

Figure 3:
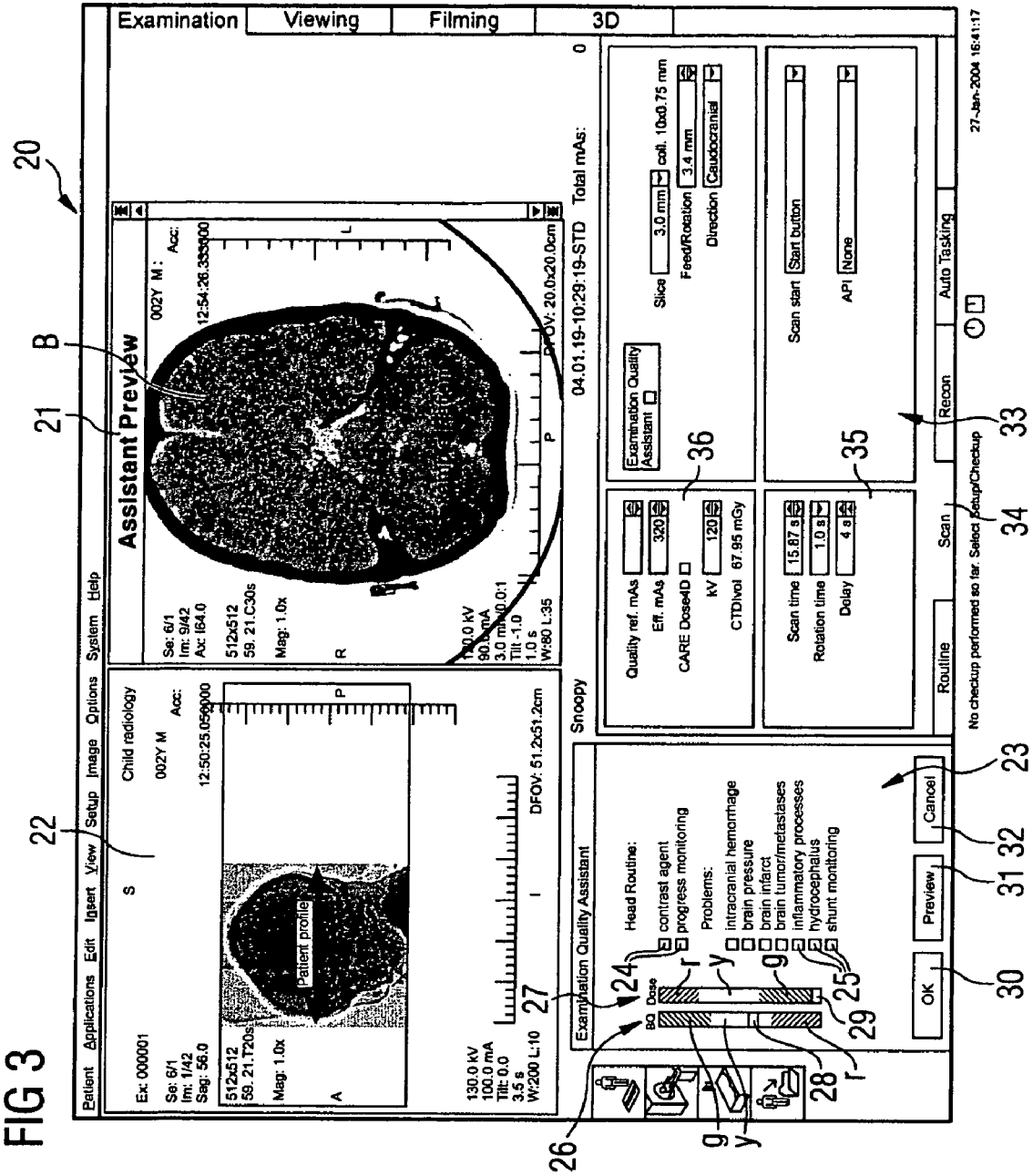
FIG. 3 shows an illustration of a user interface for displaying an example image, and of various alterable control parameters for use in methods according to at least one embodiment of the invention.

An example of such a graphic user interface is shown in FIG. 3. This graphic user interface is subdivided into various sections. Located top left is a topogram output section 22, in which at least a portion of the topogram with the region of interest, here a section through the skull of the patient, is displayed from which the profile of the patient P in this area can be recognized. Located to the right thereof is a preview output section 21 in which a current example image B is displayed.

Located below the topogram output section 22 is a first input section 23 (termed "assistant input section" 23 below), in which the operator can input, inter alia, the medical problem relevant to the examination and specific types of examination on the basis of which the examination protocol and/or the example raw data record are selected.

The assistant input section 23 and the selectable problems or types of examination are adapted in this case to the body region examined, which has been input previously when acquiring the patient data. The case of a skull examination is illustrated in FIG. 3. With such skull examinations, interest centers, for example, on whether a contrast medium examination is involved. When configuring the system, it is possible to take into account, for example, that lowering the voltage to 80 kV is sensible given the use of contrast medium and an appropriate patient profile.

Moreover, interest centers on whether progress monitoring in the case of which, if appropriate, the image data quality can be reduced by comparison with a first examination, is involved. A further interrogation item (not illustrated) can consist in whether an as yet unknown trauma is being sought. A relatively high dose would need to be used in this case.

Moreover, it could be taken into account in the system configuration that a higher proportion of metal artifacts and movement artifacts must be expected in a traumatized patient. A further interrogated item here is the search for an intracranial hemorrhage, in the case of which the dose could be lowered. The dose could likewise be reduced in the case of a brain pressure examination. Just as when searching for inflammatory processes, the dose is to be raised when a brain infarct is suspected, or when searching for a brain tumor or metastases. In the case of a hydrocephalus, examination, by contrast, the dose can be lowered dramatically. Likewise, the dose can be as low as possible in the case of shunt monitoring.

Individual interrogation boxes 24, 25 that the user can fill in to answer simply by mouse click are available for these interrogations on the user interface 20 in the assistant input section 23.

Located alongside in the assistant input section 23 are two linear regulators 28, 29 that are respectively backed by a color variation scale 26, 27.

One linear regulator 29 relates to the adjustment of the dose, while the other linear regulation 28 relates to adjusting the image quality. By displacing a linear regulator 28, 29 along the associated color variation scale 26, 27, the user inputs a change command for changing the relevant parameter. As is customary with such user interfaces, this is performed by the user employing the mouse to click on the simulated linear regulator 28, 29, and displacing the linear regulator 28, 29 with the mouse key depressed.

If the linear regulator 28 for image quality is displaced, all the control parameters are correspondingly adapted as appropriate. To this end, not only are the current strength and thus also the dose changed, but the entire spectrum of the different parameters such as, for example, the voltage, the pitch (table feed), the rotation time etc is employed. The increase in dose associated therewith is displayed automatically in this case by the linear regulator 29 being correspondingly dragged along on the dose color bar 27.

Alternatively, the user can also adjust the dose linear regulator 29 directly, and thereby carry out a dose-oriented parameter adaptation. In this case, all the control parameters are then altered according to the dose to be expected and not with the aid of the image quality to be expected, the linear regulator 28 for image quality being appropriately readjusted in order also to visualize the alteration in the image quality relative to the associated color bar 26.

In the case of this automatic adjustment of the control parameters with the aid of the linear regulators, the individual parameters of the parameter set are adapted automatically only in a sequence and way that is physically possible and clinically sensible. An incorrect input of invalid parameters is thus not possible.

Each of the color variation scales has three areas colored red r, yellow y and green g, with the aid of which it is displayed in each case whether the adjusted parameter is located inside a standard range. In this case, the standard range relates to the same types of examinations under similar conditions, that is to say with similar patient data etc. The transition between the yellow area y and the green area g respectively indicates the standard range in this case, while the red area r specifies that the respective parameter is not optimal for the relevant examination.

For example, the red area r indicates with reference to the dose parameter that an excessively high dose has been selected for the planned examination relative to other instances. In the case of the image quality parameter, by contrast, the red area r indicates that the image quality to be expected is too poor for the relevant examination. The green area g indicates that the relevant parameter can, if appropriate, even be worsened or reduced a little more, without this being disadvantageous for the planned examination. Thus, for example, it is indicated in the case of the image quality parameter that an excessively high image quality is reached that is not entirely necessary. In the case of the dose parameter, it is indicated that the dose may, if appropriate, be somewhat increased. The aim of the operator is for the parameters to lie inside the green area g in order to work with the lowest possible dose in conjunction with adequate image quality.

It is to be taken into account in this that the two indicated parameters of "image quality" and "dose" interact strongly with one another, that is to say an increase in the dose is generally also accompanied by an automatic rise in image quality and, vice versa, an increase in the image quality parameter must generally be accompanied by a rise in the dose so that an increased image quality is actually achieved. The adjustment of one of the regulators 28, 29 is consequently necessarily accompanied by an automatic displacement of the respective other regulator 28, 29. With the aid of the two regulators 28, 29 and the stored color bars 26, 27, the operator therefore directly obtains an overview as to whether the two most important mutually interacting parameters lie in an acceptable range.

The linear regulator ranges and the color ranges are respectively adapted in this case to the current selection of type of examination, patient age, attenuation calculation and/or the other clinical information. This is performed in accordance with FIG. 2 directly after the selection of the example raw data record and the selection of the starting parameter set. The adaptation of the linear regulator regions, and the selection of the starting parameter set $SP_s$ and of the example raw data record RD can also fundamentally be performed in parallel or in another sequence. This adaptation of the linear regulator ranges is performed automatically on the basis of the previously input data specific to the examination and specific to the examination object. Here, however, it is possible to configure in such a way that, for example, a radiologist can alter the automatic adaptation of the linear regulator ranges on the basis of previous experience, this then being valid for the further examinations. That is to say, an experienced radiologist can fix sensible ranges that can then be used by less experienced operators when carrying out the examinations.

Owing to the adaptation of the linear regulator ranges and the standard scales, the operator can precisely classify the currently selected image quality and the dose required for the purpose. He sees exactly whether he is using a relatively high dose for the respective case, and therefore is achieving a relatively high image quality which is possibly not at all required, or whether, for example, he is in a low limiting range of the dose, but the diagnosis could become relatively difficult because of the poor image quality.

Alternatively, the operator can also input some parameters such as, for example, the dose directly by hand, for example alphanumerically via the keyboard 17. This end is served by a second input section 33 of the user interface 20, which is arranged on the right next to the assistant input section 23 in FIG. 3. A number of so-called "index cards" can be requested in this input section 33 by clicking in the usual way on cursors 34 assigned (positioned at the lower edge of the card) to the index cards. FIG. 3 illustrates the so-called scanning card on which it is possible to input the dose (in the form of an effective tube current) and the exact tube voltage in a dose input section 36. The scan time and further time data such as the rotation time and the delay time can be input in a scan time section 35 located therebelow. The slice thickness and the slice direction can be selected directly in further input sections.

According to at least one embodiment of the invention, the image quality achieved with the current parameter adjustments can be directly visualized for the operator by compiling and displaying a corresponding example image B online on the basis of the example raw data record RD and of the current parameter set SP. To this end, the operator has to click a preview actuation section 31 in the assistant input section 23 as concluding change command.

As already mentioned, the image B is output in the preview area 21. If the operator selects the cancel actuation section 32, the inputs previously made are revised. These actuation sections 31, 32 are optional. It is possible thereby to save on computing power and to render the inputs more fluent. In the case of another example embodiment (not illustrated), the preview image is produced and illustrated directly without the interposition of operator actions in accordance with the respective parameter alterations.

The calculation of the example image B is performed in the case of the design in accordance with FIG. 1 in the image reconstruction device 12, which is also used to reconstruct the real images. However, it is also possible in principle to implement a separate example image reconstruction device on the processor.

The current exemplary image is passed on from there via the I/O interface 9 to the graphic user interface 20 of the terminal 15 and displayed there, as illustrated in FIG. 3.

There is then a wait until the system detects a user input (see FIG. 2). This user input can be, for example, an adjustment of one of the linear regulators 28, 29 for image quality or dose, or it can be a direct input of parameters on the scanning card and a subsequent activation of the preview actuation section 31 by which the operator would like to achieve a change of the current parameter set. As described above, the parameters are then appropriately changed, and a current exemplary image B for the current parameter set is immediately produced online and displayed in the preview area 21. The alteration of the parameters is performed in the case of the example embodiment in accordance with FIG. 1 in a parameter modification unit 14 that passes on the current parameter sets to the image reconstruction unit 12 so that the current exemplary image B can be calculated there in turn. There is then, again, a wait until the user makes a new input.

If the user is satisfied with the current adjustment of the parameter set and observes from the current exemplary image B that the expected image quality is sufficient for his examination, he can confirm the current parameter set and conclude the parameter input of the method by activating an confirmation section 30 ("OK"), and start image data acquisition. In this case, the image data acquisition can be performed entirely automatically after receipt of the confirmation section 30, or the actuation of a further start button or the like can further be requested.

To start a scan, that is to say image data acquisition, the parameter modification unit 14 passes on the current parameter set SP to the image data acquisition device 11, which then prompts the further measurement. If, before the activation of the confirmation field 30, the user has further input a change command without terminating the input with the activation of the preview actuation section 31, the control parameters are correspondingly changed before the image data acquisition without calculating the example image.

The abovedescribed method and the abovedescribed apparatus enable overall a parameter selection that is individually-adapted to the patient and the clinical situation, the selection of the parameters, and thus the planning of the examination, being greatly simplified overall. In the extreme case, the displacement of a single image quality regulator suffices to deliver good results. In this case, each change in parameter is presented online with regard to its effects on the image quality. Thus, even very inexperienced users are capable of preparing examinations of a quality that they actually require and wish to achieve.

In particular, such inexperienced users can therefore also carry out examinations in the limit range of image quality still just sufficient for the respective examination in conjunction with as low a dose as possible, and thus a lower burden on the patient. With such a method, the improvement or even optimization of the image quality is on a physically solid foundation, on the one hand, and on the other hand is based on the clinical experience of a team of experienced radiologists whose recommendations can be taken into account in configuring the system.

Finally, it may be pointed out once again that the preceding method which has been described in detail, and the computed tomography system illustrated are example embodiments that can be modified in the most varied way by the person skilled in the art without departing from the scope of the invention. Thus, for example, it can be provided that less experienced radiologists are offered only a dose linear regulator on the user interface for adjustment, and that no further possibilities of parameter adjustment are also available.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling an imaging modality, comprising:
    a) acquiring data specific to an examination object;
    b) automatically selecting an example raw data record from a number of example raw data records on the basis of the acquired data specific to the examination object, the example raw data records being obtained in association with one of a prior examination of the examination object and a prior examination of another examination object;
    c) producing an example image based upon the selected example raw data record, using a selected control parameter set;
    d) outputting the produced example image to a user;
    e) detecting at least one of a change command of the user to alter the control parameter set, and a confirmation command for confirming the control parameter set;
    f) changing the control parameter set in accordance with a detected change command;
    g) repeating the method steps c) to f) with the respectively current, changed control parameter set until a confirmation signal is detected; and
    h) acquiring image data by using the current control parameter set when a confirmation command is detected; wherein
    the imaging modality is a medical imaging modality and the control parameter set includes control parameters for controlling a quality of the image data acquired by the medical imaging modality.

2. The method as claimed in claim 1, wherein, in order to produce the image, an image of at least one region of interest of the examination object that has been reconstructed on the basis of the example raw data record with regard to an optimized image quality is modified as a function of the current parameter set in such a way that the image reproduces the image quality achievable with the current parameter set.

3. The method as claimed in claim 1, wherein data specific to the examination objects for use in selecting the example raw data record are determined with the aid of previously taken pictures of the examination object.

4. The method as claimed in claim 1, wherein the selection of the example raw data record is performed taking account of data specific to the examination object.

5. The method as claimed in claim 1, wherein at least a portion of the parameters of the current control parameter set are displayed to the user and offered for alteration.

6. The method as claimed in claim 5, wherein at least one of a current dose parameter and a current image quality parameter is displayed to the user and offered for alteration.

7. The method as claimed in claim 6, wherein upon detection of a dose parameter change command, the parameter set is altered automatically such that an increased image quality is achieved for a dose fixed by the dose parameter change command.

8. The method as claimed in claim 6, wherein upon detection of an image quality change command, the parameter set is altered automatically such that the current image quality is changed in accordance with the image quality change command.

9. The method as claimed in claim 1, wherein, with the display of a parameter, whether or not the relevant parameter lies in a standard range is displayed.

10. The method as claimed in claim 9, wherein the standard range is definable in advance by a user.

11. An apparatus for controlling an imaging modality, comprising:
    an interface to acquire data specific to the examination object;
    a memory device including a number of example raw data records, the example raw data records being obtained in association with one of a prior examination of the examination object and a prior examination of another examination object;
    a selection device to automatically select an example raw data record from the number of example raw data records on the basis of the acquired data specific to the examination object,
    an image reconstruction device to produce an image on the basis of the selected example raw data record and by using a selected control parameter set;
    a user interface to output the produced image to a user, and to detect a change command of the user for at least one of altering the control parameter set and detecting a confirmation command for confirming the control parameter set;
    a parameter modification device to change the control parameter set on the basis of a detected change command; and
    an image data acquisition interface to acquire image data by using a current control parameter set when a confirmation command is detected; wherein
    the imaging modality is a medical imaging modality and the control parameter set includes control parameters for controlling a quality of the image data acquired by the medical imaging modality.

12. The apparatus as claimed in claim 11, wherein the user interface comprises a graphic user interface having at least one drive device designed such that the image is displayed on the user interface for the purpose of adjusting the control parameter set, and at least a portion of the parameters of the current control parameter set is displayed to the user and offered for alteration.

13. The apparatus as claimed in claim 12, wherein the at least one drive device is designed such that at least one of a current dose parameter and a current image quality parameter is displayed to the user on the user interface and offered for alteration.

14. The apparatus as claimed in claim 12, wherein the at least one drive device is designed such that the adjustable parameters are displayed in each case in the form of a marker, adjustable with the aid of a pointer device on the user interface, the relevant parameter respectively being assigned a graphic scaling element, and the position of the marker relative to the scaling element indicating whether the relevant parameter lies in a standard range.

15. A modality having a control apparatus as claimed in claim 12.

16. The modality as claimed in claim 15, wherein the modality comprises a computer tomograph.

17. The method as claimed in claim 2, wherein data specific to the examination objects for use in selecting the example raw data record are determined with the aid of previously taken pictures of the examination object.

18. The method as claimed in claim 2, wherein the selection of the example raw data record is performed taking account of data specific to the examination object.

19. The method as claimed in claim 2, wherein at least a portion of the parameters of the current control parameter set are displayed to the user and offered for alteration.

20. The method as claimed in claim 7, wherein upon detection of an image quality change command, the parameter set is altered automatically such that the current image quality is changed in accordance with the image quality change command.

21. The apparatus as claimed in claim 13, wherein the at least one drive device is designed such that the adjustable parameters are displayed in each case in the form of a marker, adjustable with the aid of a pointer device on the user interface, the relevant parameter respectively being assigned a graphic scaling element, and the position of the marker relative to the scaling element indicating whether the relevant parameter lies in a standard range.

22. A modality having a control apparatus as claimed in claim 13.

23. The modality as claimed in claim 22, wherein the modality comprises a computer tomograph.

24. An apparatus for controlling an imaging modality, comprising:
    means for acquiring data specific to the examination object;
    means for storing a number of example raw data records;
    means for automatically selecting an example raw data record from the number of example raw data records on the basis of the acquired data specific to the examination object,
    means for producing an image on the basis of the selected example raw data record and by using a selected control parameter set;
    means for outputting the produced image to a user, and for detecting a change command of the user for at least one of altering the control parameter set and detecting a confirmation command for confirming the control parameter set;
    means for changing the control parameter set on the basis of a detected change command; and
    means for acquiring image data by using a current control parameter set when a confirmation command is detected; wherein
    the imaging modality is a medical imaging modality and the control parameter set includes control parameters for controlling a quality of the image data acquired by the medical imaging modality.

25. The apparatus as claimed in claim 24, wherein the means for outputting a produced image comprises a graphic user interface having at least one drive device designed such that the image is displayed on the user interface for the purpose of adjusting the control parameter set, and at least a portion of the parameters of the current control parameter set is displayed to the user and offered for alteration.

26. The apparatus as claimed in claim 25, wherein the at least one drive device is designed such that at least one of a current dose parameter and a current image quality parameter is displayed to the user on the user interface and offered for alteration.

27. The apparatus as claimed in claim 25, wherein the at least one drive device is designed such that the adjustable parameters are displayed in each case in the form of a marker, adjustable with the aid of a pointer device on the user interface, the relevant parameter respectively being assigned a graphic scaling element, and the position of the marker relative to the scaling element indicating whether the relevant parameter lies in a standard range.

28. A modality having a control apparatus as claimed in claim 24.

29. The modality as claimed in claim 28, wherein the modality comprises a computer tomograph.

30. A computer program embodied on a tangible computer readable medium, adapted to, when executed on a computer, cause the computer to carry out the method as claimed in claim 1.

31. A computer program product, including the computer program of claim 30.

32. A tangible computer readable medium including program segments for, when executed on a computer, causing the computer to implement the method of claim 1.

* * * * *